United States Patent [19]

Inguaggiato et al.

[11] Patent Number: 5,304,208
[45] Date of Patent: Apr. 19, 1994

[54] CARDIOSTIMULATOR DEVICE OF THE RATE-RESPONSIVE TYPE

[75] Inventors: Bruno Inguaggiato, Milan; Giorgio Corbucci, San Giovanni in Persiceto, both of Italy

[73] Assignee: Sorin Biomedica S.p.A., Saluggia, Italy

[21] Appl. No.: 886,073

[22] Filed: May 20, 1992

[30] Foreign Application Priority Data

May 21, 1991 [IT] Italy ............................ TO91A000376

[51] Int. Cl.$^5$ .............................................. A61N 1/00
[52] U.S. Cl. ...................................................... 607/17
[58] Field of Search ............ 128/419 PG, 419 D, 782; 607/9, 14, 17, 18, 19

[56] References Cited

U.S. PATENT DOCUMENTS 4,936,304  6/1990  Kresh et al. .................. 128/419 PG

OTHER PUBLICATIONS

AAMI 17th Annual Meeting, May 9-12, 1982, San Francisco, "An Interactive Microcomputer-based Graphic System for Analysis of Cardio-Dynamic Function".
Invited Speaker at 35th ACEMB Conference: Stimulation, Sensing, and Biocompatibility of Implanted Devices, Sep. 1982, "Pacing Sensors For Heart-Rate Control and Biophysical Telemetry", pp. 1-4.
Progress in Artificial Organs-1983, "Effects of Left Ventricular Bypass on Intramyocardial Mechanics", Kresh et al., pp. 107-116.
Heart Transplantation/Volume IV, No. 2, Feb. 1985, Organ Procurement & Organ Preservation, "The Intramyocardial Pressure", Kresh et al., pp. 241-264.
American College of Surgeons, 1985, Surgical Forum, vol. XXXVI, Kresh et al., "Continuous Intraoperative Monitoring of Myocardial Tissue Pressure: Experimental & Clinical Results", pp. 301-303.
Journal of Applied Physiology, Mar. 1993, vol. 74, No. 3, "Ultrasonic Measurements *In Vivo*".
Sensor Review, vol. 13, No. 1, 1993, pp. 22-25; MCB University Press, Canhui Cai et al., "A Versatile Ultrasonic Ranging System".

*Primary Examiner*—Lee S. Cohen
*Assistant Examiner*—Marianne Parker
*Attorney, Agent, or Firm*—George Hoare, Jr.

[57] ABSTRACT

A cardiostimulator device includes an accelerometric sensor positioned on the electrode or cathetar intended to be inserted in the cardiac mass, possibly being associated with a stimulating or sensing electrode. In this way, it is possible to regulate the frequency (and in general all the methods) of stimulation in dependence on the so-called natural heart acceleration correlated to the physical activity of the patient.

13 Claims, 2 Drawing Sheets

CARDIOSTIMULATOR DEVICE OF THE RATE-RESPONSIVE TYPE

FIELD OF THE INVENTION

The present invention relates to cardiostimulator devices of the type currently known as "pacemaker".

More specifically, the invention relates to pacemakers of the so-called "rate-responsive" type, in which the characteristics of the stimulation can be varied in dependence on one or more parameters correlated with the physical activity of the person to whom the pacemaker is fitted.

DESCRIPTION OF THE PRIOR ART

In particular, electrostimulator devices are known in the art which are controlled by the venous blood temperature (U.S. Pat. No. 4,726,383), by the blood oxygen saturation (U.S. Pat. No. 4,807,629), by the respiratory frequency (U.S. Pat. No. 4,567,892), by the so-called "minute ventilation" (U.S. Pat. No. 4,596,251), by the blood p.H (U.S. Pat. No. 4,009,721), or by vibrations (typically of the order of 5-50 Hz) transmitted to the pacemaker during physical activity (U.S. Pat. No. 4,428,378).

Other devices available on the market utilise the low frequency component of acceleration (0-4 Hz) characterising the movements of the human body as the parameter. In this respect reference can be made, for example, to U.S. Pat. No. 4,428,378 and to the corresponding European Patent Application 0,080,348, or yet to European Patent Application, 0,259,658.

European Patent Application 908300437, in the name of the same Applicant, also deals essentially with such an arrangement and describes an accelerometric sensor which can generate a signal indicative of the activity of the person fitted with the stimulator by detecting the deformations induced by this activity in the shape of a mass of mercury.

Commercially available electrostimulators based on the detection of accelerometric signals by different methods include that sold by Sorin Biomedica S.p.A under the trade name "SWING 100", that sold by C.P.I. under the trade name "EXCEL" and that sold by Intermedics under the trade name "DASH". In devices based on vibrations (5-50 Hz) and on accelerations (0-4 Hz), the sensor is primarily inserted in the electrostimulator and is therefore sensitive solely to the stresses to which the whole human body is subject and is entirely insensitive to the mechanical phases of the cardiac cycle in the sense that the systolic and diastolic mechanical cardiac cycle has absolutely no influence on the sensor.

Pacemakers of the rate-responsive type also exist in which, as a parameter indicative of the physical activity of the person to which it is fitted, quantities are utilised which derive from stimulation of sympathetic tonus which increases in proportion to an increase in physical activity as well as being increased by the effect of drugs and emotional stress.

Other rate-responsive electrostimulators are known which utilise one of the physiological parameters which vary with variations in sympathetic tonus stimulation as the signal for adjusting and controlling the frequency of stimulation. Such parameters are of electrocardiological type, such as the Q-T interval detected as the time interval between the stimulating impulse and the T-wave, the ventricular depolarisation gradient and others. Parameters derived from electrocardiological and cardiomechanical signals have also been used, for example, the interval between the electrical stimulus output by the pacemaker and the mechanical contraction of the heart detected by methods based on the variation in impedance between electrodes positioned internally and/or externally of the cardiac chamber. Finally, exclusively cardiomechanical parameters have been used, such as, for example, the variations in volume of the right ventricle and its contractility deduced from the first derivative of the ventricular volume, where the volume measurements are again based on the detection of impedance variations between intercardiac electrodes.

Furthermore, the maximum value of the first derivative of the right ventricular pressure, which is closely related to the cardiac contractility and which requires a pressure sensor in correspondence with, or contiguous to, the ventricular-stimulation electrode is of cardiomechanical type. Such parameters and their associated methods of detection are utilised in various electrostimulators which are currently on the market or in an advanced state of clinical experimentation.

For example, the stimulators sold under the trade name "PRISM" by the company Cordis utilise electrocardiological parameters (ventricular depolarisation gradient), as do devices sold under the trade names "QUINTECH" and "RHYTHMIX" by the company Vitatron (Q-T interval). Alternatively, the stimulator sold under the trade name "PRECEPT" by the company CPI and the device sold under the trade name "INOS" by Biotronic utilise a parameter of the electrocardiological-cardiomechanical type (pre-ejection interval). Finally, in addition to the product "PRECEPT" mentioned above, the device sold under the trade name "DELTATRAX" by the company Medtronic utilises parameters of the cardiomechanical type (specifically, the so-called "Stroke Volume" is used) (dP/dt max, that is the maximum value of the first temporal derivative of the right ventricular pressure).

It should, however, be noted that the said devices have significant limitations in practice.

For example, for measurement of the time intervals and amplitudes, apparatus based on electrocardiological or electrocardiological-cardiomechanical parameters make reference to the cardiac event caused by the electrical stimulation, with the use of the temporal phases of the electrical stimulation pulse as a reference, which necessitates autocalibration when the spontaneous cardiac activity alternates with that controlled by the pacemaker.

Apparatus based on cardiomechanical parameters, such as the volume and its first derivative with respect to time, are limited by the method of measurement based on the impedance variations of intracardiac electrodes which could provide reliable parameters only on the clinically impossible hypothesis of a right ventricular cavity which can be represented by a solid of rotation with the catheter strictly coincident with the axis of rotation thereof.

Finally, the measurement, made with a pressure sensor positioned close to the ventricular-stimulation electrode, of the maximum value of the first derivative of the right ventricular pressure as an index of contractility, demonstrates, in experimental clinical applications, a limitation due to the possibility of the sensor becoming encapsulated by the myocardiac tissue with the result that the precision of the measurement is compromised since this must take place with the sensor membrane in direct contact with the blood.

OBJECTS AND SUMMARY OF THE INVENTION

The object of the present invention is, therefore, to provide a cardiostimulator device which is capable of overcoming the disadvantages typical of the prior known arrangements and, in particular:

in the case of sensor based on ventricular pressure, the disadvantages resulting from the encapsulation of the pressure sensor in the myocardial tissue or from contiguity with an anatomic structure in rapid movement, which can cause changes in the deformation of the sensor membrane from which the pressure signal originates and, in the case of measurement by methods based on the variation in impedance of the ventricular ejection volume of its derivative, the disadvantages resulting from the lack of precision or false signals induced by the complex structure of the right ventricular cavity and by the relative position of the electrode being different from that hypothesized for a volume of a solid of rotation whose axis is coincident with the catheter.

According to the present invention, this object is achieved by a cardiostimulator device having the characteristics set out specifically in the following claims.

In summary, the cardiostimulator according to the invention is based on the idea of utilising the Natural Heart Acceleration, or NHA, as the physiological parameter for controlling the adaptation of the stimulation characteristics to the physical activity.

More specifically, the present invention utilises, either as a sole reference parameter of the physical activity or as one of the parameters associated with others, the acceleration to which the cardiac mass is subjected by reaction both to the atrial and to the ventricular contractile phases of the heart, measured by an accelerometric sensor positioned in one of the cardiostimulator electrodes or leads inserted in the chambers of the heart.

This sensor can be made by any available technology: for example, it may be an accelerometric sensor of piezoelectric type, piezoresistive, capacitive, inductive or magnetic (Hall effect) type or it may be achieved by an evaluation of the impedance variations in a conductive fluid which is deformed by the effect of the acceleration.

Depending on the type of sensor used the electronic preamplification will or will not be performed in the body of the electrode which contains the sensor and, as a rule, this will be obligatory in the case of sensors having a high output impedance, (greater than 1 Megaohm), as for example in piezoelectric sensors. The electronic preamplification circuit will naturally be related to the type of sensor used and will be more fully explained below.

DESCRIPTION OF THE APPENDED DRAWINGS

The invention will now be described purely by way of nonlimiting example, with reference to the appended drawings, in which:

FIG. 3b is a graph depicting change in pressure of the left ventricle over the same period of time as FIG. 3a.

DETAILED DESCRIPTION OF THE INVENTION

Figure 1:
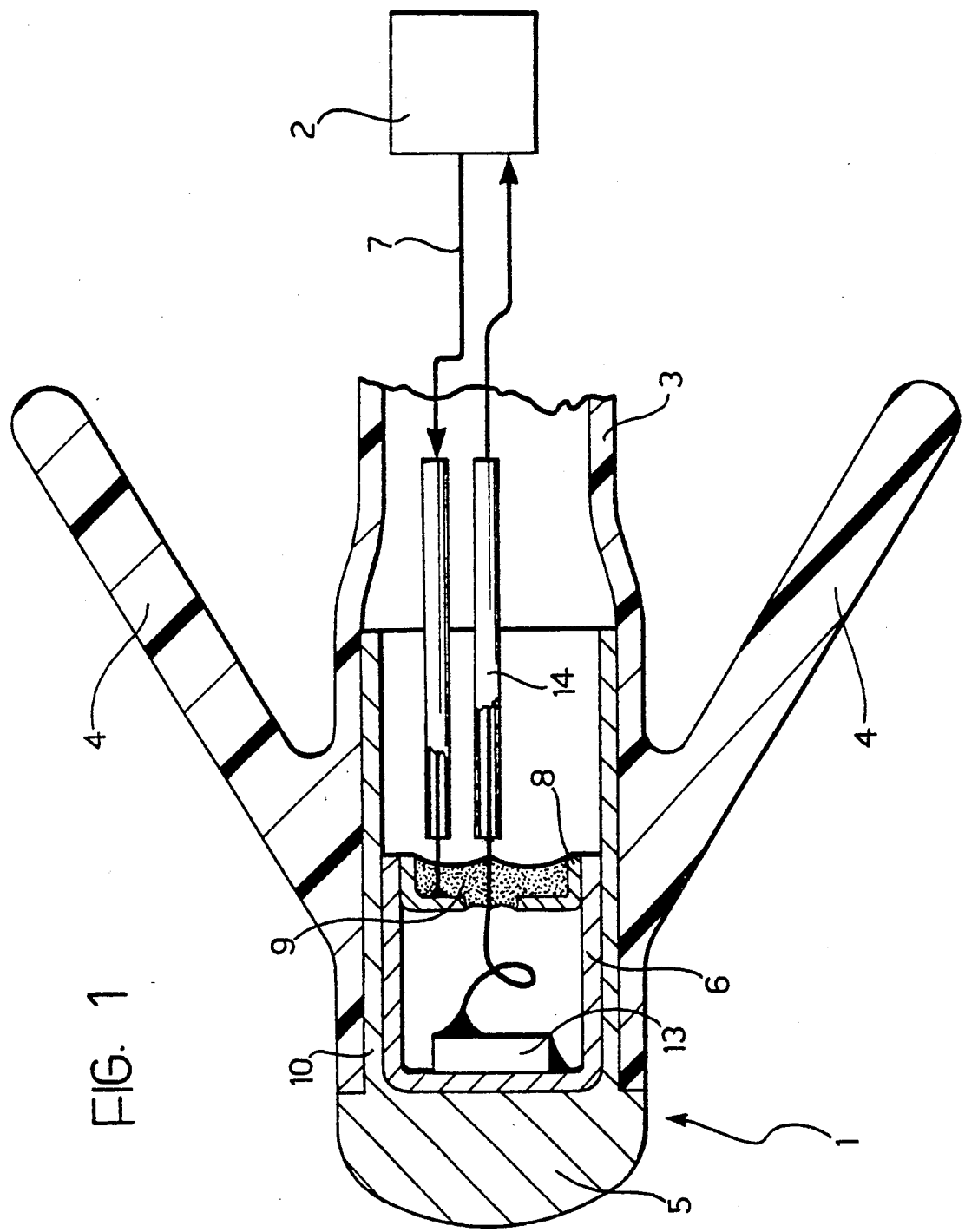
FIG. 1 is a partial schematic view of a first embodiment of a sensor intended to be used in a device according to the invention.
Figure 2:
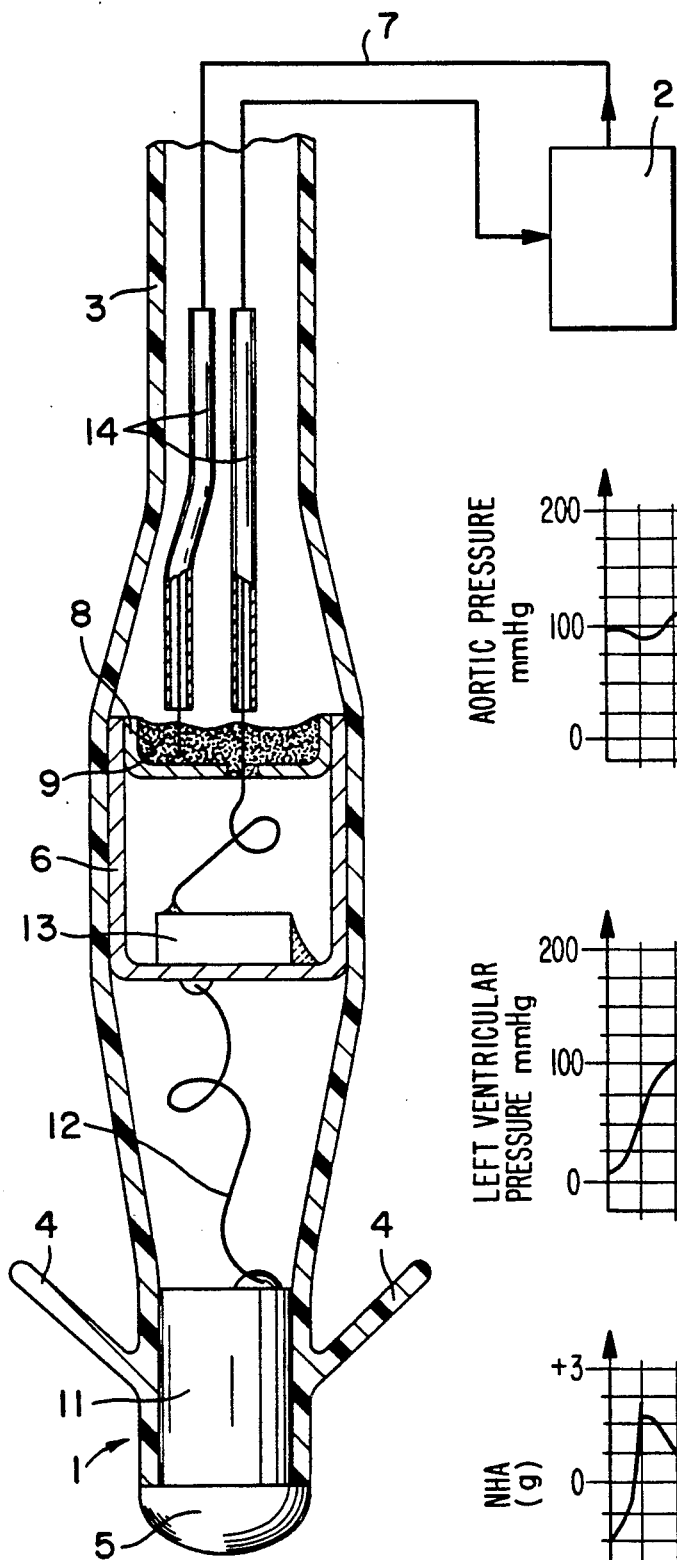
FIG. 2 is a schematic view of a second embodiment of a sensor intended to be used in a device according to the invention.

More specifically, FIGS. 1 and 2 illustrate the end part or tip of a stimulation electrode or catheter (lead) of a cardiostimulator device of the rate-responsive type.

In the drawings, the electrode is indicated with the reference number 1, while the circuit assembly of the cardiostimulator device is generally indicated in the form of an operative block 2.

In this connection it should be noted that the circuit assembly 2 can be made in accordance with widely different technical solutions: the whole according to criteria well known to the expert in this art, and which do not therefore need to be explained specifically in the present description, above all these not being essential and/or relevant for the purposes of an understanding of the invention.

In essential terms, the electrode 1, and in particular the point or tip illustrated in FIGS. 1 and 2, comprises essentially a generally tubular insulating sheath 3 of material having good characteristics of biocompatibility. From the insulating sheath 3 extend a plurality of tines 4 for fixing the electrodes in the cardiac tissue.

Fitted into the distal end of the sheath 3 is a stimulation tip 5 of metal (for example, titanium or other material having good biocompatibility characteristics) intended to perform the actual stimulation of the cardiac muscle. Reference 6 indicates a rigid metal containment capsule which is in electrical contact with the tip 5 and with a conductor 7 which conveys the stimulation signal intended to be applied to the heart from the circuits of the block 2.

Preferably the conductor 7 is connected to an end wall 8 of the containment capsule 6 facing the proximal end of the electrode 1. For this purpose the end wall 8 has a cladding 9 of ceramic material which serves as a ceramic passage element.

In the case of the embodiment of FIG. 1, the capsule 6 is fitted directly into the stimulation tip 5 in electrical contact therewith. More specifically, in the embodiment of FIG. 1 the point or tip 5 is of approximately hemispherical or solid dome shape. It is provided with a tubular collar 10 which engages within the sheath 3 and houses the capsule 6, which is pushed into the collar 10 until it bears against the bottom wall of the tip 5.

In the embodiment of FIG. 2 on the other hand, the capsule 6 is located at a certain distance from the tip 5. In this case the collar of the latter, indicated 11, may be a solid cylinder connected by a conductor 12 to the body or casing of the capsule 6 which is located at a certain distance from the tip 5 within the sheath 3.

With the arrangement of FIG. 1, the tip 5 and, in particular, its collar 10, is generally larger than the capsule 6 which must be housed within the collar 10.

On the other hand, the arrangement of FIG. 2 does not impose specific dimensional limitations on the tip 5.

The capsule 6 is in fact spaced from this so that the dimensions of the tip 5 can be chosen freely, it being made smaller in dependence on the specific applicational requirements and the capsule 6 being located instead in a widened intermediate portion of the sheath 3 which will therefore have a general swelling or entasis.

In both embodiments, within the capsule 6 (which, as has been mentioned, is rigid and therefore substantially indeformable), is an accelerometric sensor element 13 which is connected to the circuit block 2 through a conductor 14 which extends from the capsule 6 through the sheath 3.

As already mentioned, the sensor 13 can be an accelerometric sensor formed by any available technology: piezoelectric, piezoresistive, capacitive, inductive, magnetic (for example, Hall effect) or else formed through evaluation of impedance variations in a conductive fluid which is deformed by the effect of the acceleration.

This sensor has associated with it, preferably within the capsule 6 an electronic preamplification and amplification network (which can be obtained using current circuit integration technology), adapted to the type of sensor used.

For example, in the case of a piezoelectric type accelerometric sensor, a so-called voltage follower, or rather a so-called load amplifier, could be used. In the case of piezoresistive sensors, or those based generally on variations in impedance, it may be necessary to supply the transducer with dc (continuous or pulsed) and to amplify the voltage developed across the terminals of the transducer itself.

In each case, the accelerometric sensor 13 is disposed in a substantially indeformable capsule located on the electrode 1 which is intended to be fitted within the cardiac mass so as to be naturally sensitive to the Natural Heart Acceleration (NHA).

Figure 3A:
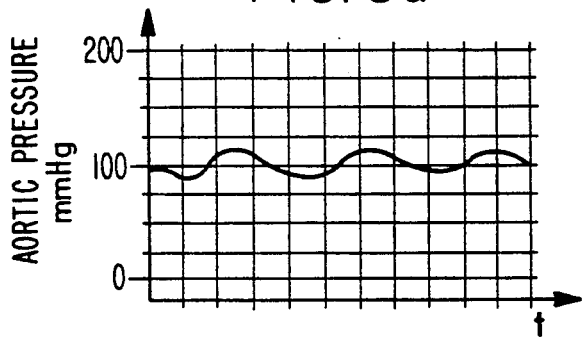
FIG. 3a is a graph depicting the change in aortic pressure over time.
Figure 3B:
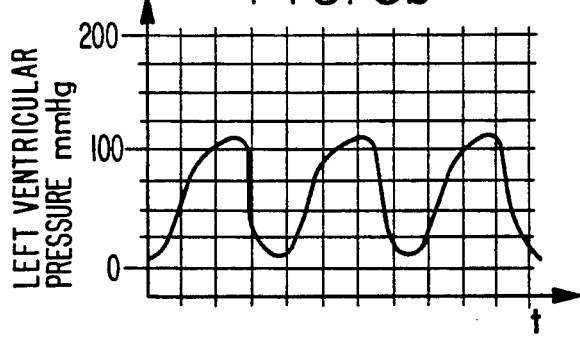
Figure 3C:
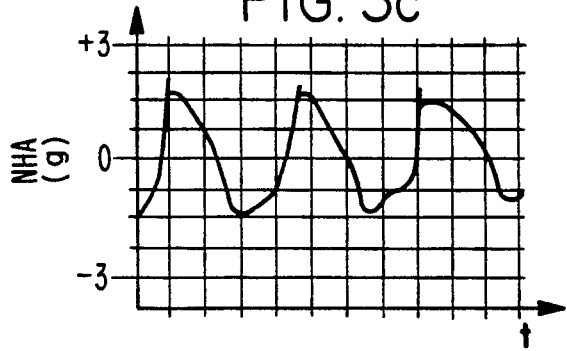
FIG. 3c is a graph depicting the change in Natural Heart Acceleration over the same period of time as FIGS. 3a and 3b.

The variation in this parameter (measured in g) is illustrated schematically in the diagram of FIG. 3c), in comparison with corresponding signals of aortic pressure (in mm of mercury—FIG. 3a) and left ventricular pressure (again in mm of mercury—FIG. 3b) measured on a natural heart. All this is in the terms described, for example, in the article "Characterisation of Natural and Total Artificial Heart Acceleration" by Pantalos, Kim, Robinson, Everett and Olsen published in volumne XXV of the Transactions of the American Society Artificial Internal Organs 1989. Similar data have been detected experimentally by the Applicant for the purpose of demonstrating the variations in the maximum NHA caused by a drug ("Dopamine") which has a stimulating effect on cardiac contraction which simulates physical activity.

The substantial advantage demonstrated by the solution of the invention compared, for example, with solutions based on the detection of the temporal derivative of cardiac pressure is the absolute insensitivity of the acceleration sensor 13 to deformations or compressions which may be caused by the cardiac tissue. On the contrary, it differs from pressure sensors which must necessarily have a part which is deformable under pressure, in that acceleration sensors needing to be sensitive solely to inertial forces, can be located in an entirely rigid capsule (the capsule 6) constituting an integral part of an electrode or catheter inserted in the ventricle or in the right atrium.

The sensor 13 is thus entirely insensitive to the pressure in the ventricle or the right atrium or to movements and deformations of the myocardial wall, and to pressure which the cardiac wall can exert, particularly on the distal electrode.

On the other hand, in arrangements which require the provision of a deformable membrane so as to achieve a transducing action on the blood pressure or on the force exerted by the tissues during contraction against the sensor, any alteration in the working conditions of this deformable membrane (such as those consequent on an encapsulation of the sensor by part of the cardiac tissue) causes an undesirable change in the function of the sensor, and therefore in the stimulation action, which is difficult to predict.

It should, moreover noted that the pressure signal, which represents the useful signal for the said known prior art sensors, is not used in any way for measuring NHA. This is because, in these sensors based on the detection of the pressure signal, the useful signal is derived from the detection of the blood pressure or, in any case, from the detection of a force applied directly by the myocardium to a membrane which, upon deforming, activates a transducer (piezoelectric, piezoresistive, etc).

Contrary to this, in the arrangement of the invention, the transducer is completely isolated from its surrounding environment and the force which acts on it derives solely from the inertial force applied by a mass positioned within the capsule, directly on the sensitive element which is constituted by an electrode which is connected to the cardiac tissue and, in fact, very often encapsulated thereby (a phenomenon which in the arrangement of the invention does not cause any problems).

The arrangement of the invention thus makes it possible to measure, in a particularly precise and reliable manner, the acceleration to which the cardiac mass is subjected as a reaction to any contractions whatsoever, whether left or right atrial, or combined ventricular contractions. Under this aspect, given the fact that the magnitude of the reaction of the cardiac mass (that is, in practice, the NHA) is correlated to the speed and volume both of the atrial and ventricular ejection in different phases, one deduces that this parameter provides very much further and more interesting indications of the physical activity of the person fitted with the device than is provided by the detection of a pressure signal.

This means that a sensor based on the present invention lends itself particularly well to being used as a sole signal source for modulation of the stimulation characteristics. Naturally this does not exclude the possibility that a device of the invention could have other sensor elements associated therewith for detecting other physiological parameters for modulating the stimulation characteristics.

In particular, the circuit block 2 (which constitutes the body of the pacemaker itself) can be configured (in a manner known per se) so as to measure, and possibly process, as more fully explained below, the natural cardiac acceleration signal measured in the right ventricle, in the right atrium or in both cavities simultaneously.

The signal in question can be processed in several different ways such as, for example, by identifying its peak value or else by calculating its average value and, in general, in such a way as to achieve all the mathematical processing capable of having a significance with regard to effecting the stimulation, such as, for example the possibility of identifying in a single NHA signal the accelerometric characteristics of the systolic phases of both the atrium and the ventricle.

The arrangement of the invention can be applied to any type of implant device which can correct cardiac arhythmia, including therefore in this group single-chamber stimulation pacemakers, twin-chamber pacemakers, pacemakers for control of tachycardia and implantable defibrillators. In particular, the invention can be used for electrostimulators which regulate the frequency and the manner of stimulation by synchronizing themselves with the spontaneous activity of the atrium and/or of the ventricle by processing an NHA signal which includes the effects both of the ventricular and the atrial contraction.

Naturally, the principle of the invention remaining the same, the details of construction and the embodiments can be varied widely with respect to what has been described and illustrated, without departing from the scope of the present invention.

What is claimed is:

1. A cardiac stimulator device, comprising:
   a) means for detecting a natural heart acceleration of a user and for generating a signal representative thereof; and
   b) means for stimulating the heart of the user as a function of said natural heart acceleration signal.

2. The device of claim 1, wherein said detecting means comprises at least one electrode inserted into the heart of the user and an accelerometric sensor operatively associated with said electrode.

3. The device of claim 2, wherein said accelerometric sensor is mounted on said at least one electrode.

4. The device of claim 1, further comprising control means for controlling variation in the stimulation of the heart, wherein said control means receives said natural heart acceleration signal and generates said representative signal dependent upon said natural heart acceleration signal.

5. The device of claim 1, further comprising means for detecting physical activity of the user and for generating a signal representative thereof, and means for controlling variation in the stimulation of the heart, wherein said control means is dependent upon said natural heart acceleration signal and said physical activity signal.

6. The device of claim 1, further comprising means for processing said natural heart acceleration signal, wherein said processing means is adapted for identifying a peak value of said natural heart acceleration.

7. The device of claim 1, further comprising means for processing said natural heart acceleration signal, wherein said processing means is adapted for detecting said signal corresponding to the right ventricle, or the right atrium, or simultaneously from both.

8. The device of claim 1, wherein said device comprises means for pacemaker acting upon a single chamber of the heart.

9. The device of claim 1, wherein the device comprises means for pacemaker acting upon two chambers of the heart.

10. The device of claim 1, wherein the device comprises means for controlling tachycardia.

11. The device of claim 1, wherein said stimulating means further comprises an implantable defibrillator.

12. The device of claim 1, further comprising means for processing said natural heart acceleration signal, wherein said processing means is adapted for calculating an average value of said natural heart acceleration.

13. The device of claim 1, further comprising means for processing said natural heart acceleration signal, wherein said processing means is adapted for identifying accelerometric characteristics of atrial and ventricular systolic phases from said natural heart acceleration signal.

* * * * *

UNITED STATES PATENT AND TRADEMARK OFFICE
CERTIFICATE OF CORRECTION

PATENT NO. : 5,304,208
DATED : April 19, 1994
INVENTOR(S) : Bruno Inguaggiato, Giorgio Corbucci It is certified that error appears in the above-indentified patent and that said Letters Patent is hereby corrected as shown below:

Column 8, Line 23: delete "pacemaker"

Signed and Sealed this

Twentieth Day of September, 1994

Attest:

BRUCE LEHMAN

Attesting Officer     Commissioner of Patents and Trademarks